United States Patent [19]

Hübner et al.

[11] 4,107,152
[45] Aug. 15, 1978

[54] POLYURETHANES PRODUCED FROM PHOSPHORUS CONTAINING FLAME RETARDING AGENTS WHICH ARE REACTIVE WITH ISOCYANATES

[75] Inventors: Hans Hübner, Leverkusen; Johannes Blahak, Cologne; Hans-Joachim Meiners, Leverkusen, all of Fed. Rep. of Germany

[73] Assignee: Bayer Aktiengesellschaft, Leverkusen, Fed. Rep. of Germany

[21] Appl. No.: 829,833

[22] Filed: Sep. 1, 1977

Related U.S. Application Data

[62] Division of Ser. No. 637,630, Dec. 4, 1975, Pat. No. 4,061,697.

[30] Foreign Application Priority Data

Dec. 17, 1974 [DE] Fed. Rep. of Germany ....... 2459491

[51] Int. Cl.² ............................................. C08G 18/32
[52] U.S. Cl. ...................................... 528/68; 521/165
[58] Field of Search ................... 260/2.5 AM, 2.5 AJ, 260/77.5 AM, 75 NH

[56] References Cited

U.S. PATENT DOCUMENTS

| | | | |
|---|---|---|---|
| 3,681,290 | 8/1972 | Meckel | 260/77.5 AM |
| 3,794,621 | 2/1974 | Meckel | 260/77.5 AM |
| 4,061,697 | 12/1977 | Hübner | 260/2.5 AM |

*Primary Examiner*—C. Warren Ivy
*Attorney, Agent, or Firm*—Gene Harsh; Joseph C. Gil; William E. Parry

[57] ABSTRACT

This invention relates to novel flame retarding agents and processes in which they are used in the production of polyurethanes. These compounds are represented by the general formula:

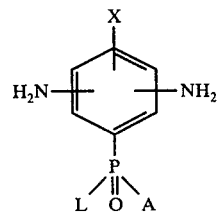

wherein:
A and L, which are identical or different, represent optionally branched $C_1$-$C_{17}$-alkyl groups or -OR groups wherein R represents an optionally branched $C_1$-$C_8$-alkyl group, and X represents hydrogen, halogen, an optionally branched $C_1$-$C_8$ alkyl group, a $C_6$-$C_{12}$ aryl or aralkyl group, $NH_2$, $CF_3$, CN, COOR', $SO_3R'$,

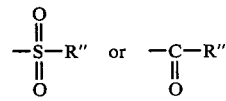

wherein:
R' represents hydrogen or an optionally branched alkyl or cycloalkyl group having 1–10 C atoms and
R" represents an optionally branched alkyl or cycloalkyl group having 1–10 C atoms.

6 Claims, No Drawings

POLYURETHANES PRODUCED FROM PHOSPHORUS CONTAINING FLAME RETARDING AGENTS WHICH ARE REACTIVE WITH ISOCYANATES

This is a division of application Ser. No. 637,630 filed Dec. 4, 1975, now U.S. Pat. No. 4,061,697.

BACKGROUND OF THE INVENTION

It is known that the flame resistance of synthetic resins and in particular polyurethane resins can be increased by adding unreactive low molecular weight phosphoric or phosphonic acid esters to them during their preparation. This procedure is, however, limited by the fact that if the desired mechanical properties are to be obtained, only limited quantities of low molecular weight compounds may be added, such quantities being insufficient for complete flame protection. The procedure is also limited by the fact that the additives tend to migrate from the resin due to their low molecular weight.

Attempts have been made to overcome this difficulty by incorporating halogen-containing polycarboxylic acids or polyhydroxyl compounds into the molecular structure. Halogenated components of this kind include, for example, tetrachlorophthalic acid, dibromophthalic acid and hexachloroendomethylene tetrahydrophthalic acid. Although the flame resistance of polyesters prepared from such components is substantially improved, for example, after they have been foamed with polyisocyanates, it is still insufficient in many cases. Other disadvantages lie in the fact that these polyesters are difficult to mix with polyisocyanates at room temperature because of their high viscosity. Processing difficulties then occur during the production of foams. Moreover, these polyesters frequently give rise to brittle foams so that they can only be converted into foams having good mechanical properties if they are first blended with the conventional polyesters. However, in that case, the flame resistance is partly lost. Moreover, many of the conventional halogen containing flame retarding agents liberate corrosive gases such as hydrogen chloride or hydrogen bromide on combustion.

Flame resistant polyurethane resins having good mechanical properties can be obtained when using polyisocyanates which contain phosphoric acid or thiophosphoric acid groups, e.g. phosphoric acid (p-isocyanatophenyl)-triesters. The phosphoric ester triisocyanates used can, however, only be obtained by multistage processes and their use is therefore often uneconomical.

Hydrocarbon phosphonyl diisocyanates have also been used for the production of flame resistant foams. These diisocyanates, however, are acylisocyanates which are not only physiologically undesirable because of their odor and vapor pressure but which are also particularly undesirable because of their excessive reactivity and the ease with which they can be saponified. Thus, usable foams can be obtained from them only if they are mixed with considerable proportions of conventional polyisocyanates such as tolylene diisocyanate. It is obvious, of course, that in that case, they lose their flame retarding properties.

It is also known in the art that phosphorus containing polyethers and polyesters can be used for the production of polyurethane foams. The products, however, produce fumes in considerable quantities when exposed to heat. Moreover, in many cases they are difficult to process because of their viscosity which can give rise to difficulties in foaming.

DESCRIPTION OF THE INVENTION

It has now been found that non-flammable or substantially non-flammable polyurethane resins can be obtained without the disadvantages generally involved with using the known flame retarding agents mentioned above by utilizing novel aromatic dialkylphosphonic acid esters which are amino substituted on the nucleus as reactants for the preparation of the polyurethane.

This invention therefore relates to flame retarding agents of the following formula which are reactive with isocyanates:

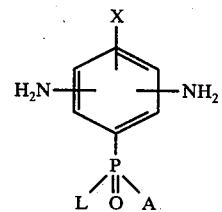

wherein:
A and L which may be identical or different, represent optionally branched $C_1$-$C_{17}$ (preferably $C_1$-$C_8$ alkyl groups) or OR groups, R representing an optionally branched alkyl group and preferably R representing an optionally branched $C_1$-$C_8$ alkyl group and X represents hydrogen, halogen (preferably Cl or Br), an optionally branched $C_1$-$C_8$-alkyl group, a $C_6$-$C_{12}$ aryl or aralkyl group. $NH_2$, $CF_3$, $CN$, $COOR'$, $SO_3R'$,

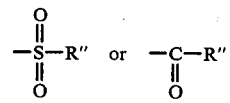

wherein:
R' represents hydrogen or an optionally branched alkyl or cycloalkyl group having 1-10 C atoms, and
R" represents an optionally branched alkyl or cycloalkyl group with 1-10 C atoms.

The polyamines which are particularly preferred according to the invention are those of the above general formula in which:
R represents a branched or straight chain $C_1$-$C_4$-alkyl group; and
X represents hydrogen, chlorine, $CH_3$, $NH_2$ or $COOR'$;
R' represents a branched or straight chain $C_1$-$C_4$-alkyl group.

The following are typical examples of the compounds according to the invention:

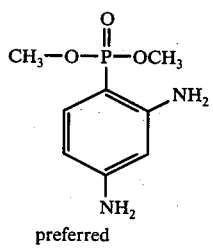
preferred

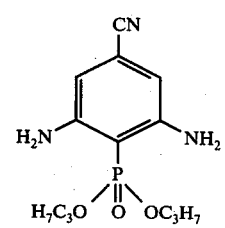

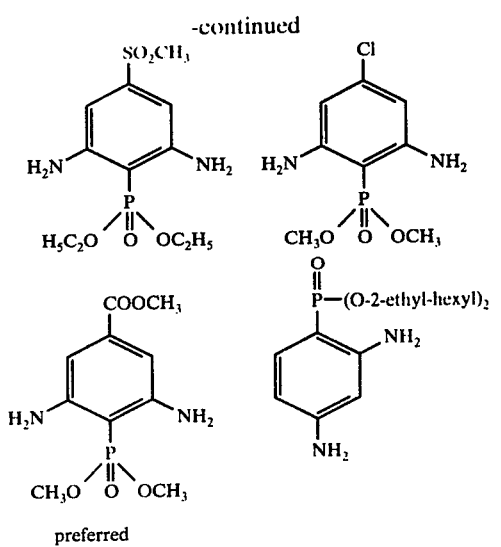
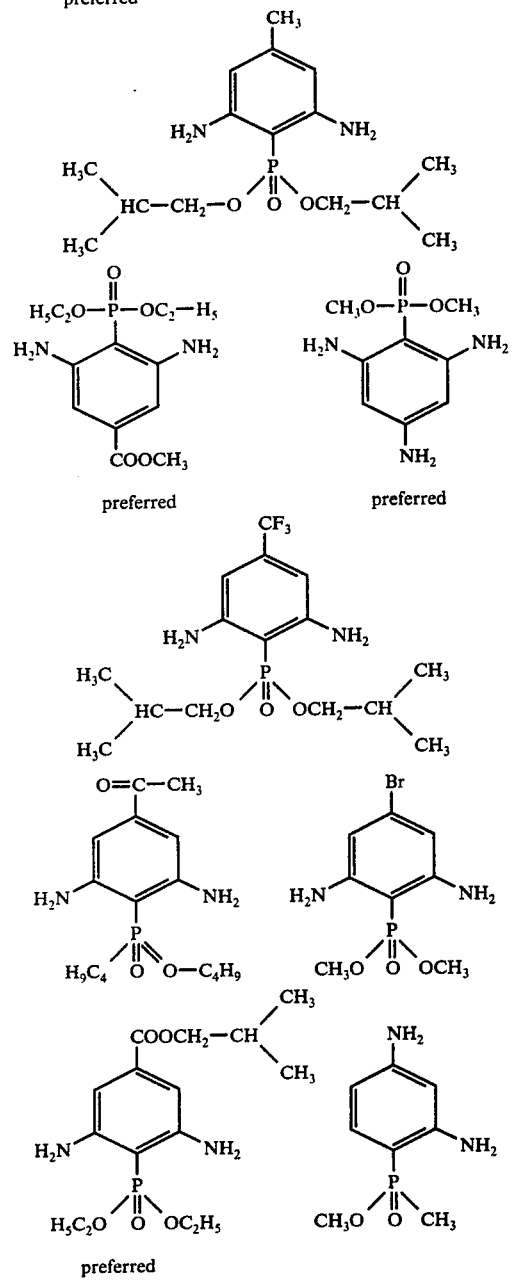
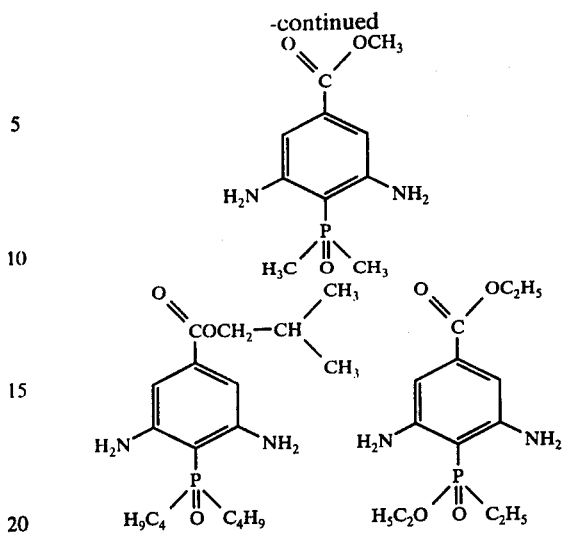
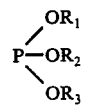

These compounds are prepared by catalytic reduction of the corresponding polynitro precursors in the pressure of Raney nickel at pressures of 30 to 100 excess atmospheres, preferably 50 to 80 excess atmospheres and temperatures of 20° to 120° C, preferably 35 to 65° C, using as a solvent, the alcohol which corresponds to the radical R in the phosphinic or phosphonic acid ester. According to an earlier proposal by the present applicants (German Offenlegungsschrift 24 21 070, corresponding to British Patent Application No. 17723/75), the polynitro compounds corresponding to the polyamines according to the invention can be obtained in high yields and practically free from by-products by a modified Michaelis-Arbusov reaction between aromatic halogen compounds which contain nitro groups and phosphorous acid alkyl esters or phosphonus or phosphinous acid alkyl esters.

Phosphorous acid esters suitable for the reaction are those of the general formula:

$$P\begin{array}{c}-OR_1\\-OR_2\\-OR_3\end{array}$$

wherein $R_1$, $R_2$ and $R_3$ which may be identical or different represent optionally branched $C_1$-$C_8$ alkyl groups. It is preferred, however, to use the trimethyl and triethyl esters because in that case the alkyl halides produced in the reaction have a low vapor pressure and can therefore be continuously removed from the reaction mixture.

The solvents which are optionally used may be halogenated hydrocarbons, particularly toluene or xylene; or ethers, preferably dioxane; or nitriles, preferably acetonitrile; as well as other solvents which do not react with the activated aromatically bound halogen or with the phosphorous acid alkyl esters, for example dimethylformamide or dimethylsulphoxide.

Catalysts may be added to accelerate the reaction. The catalysts which may be used include e.g. tertiary amines such as triethylamine, tributylamine, N-methylmorpholine, N-ethylmorpholine, N-cocomorpholine, N,N,N',N'-tetramethylethylenediamine, 1,4-diaza-bicyclo-(2,2,2)-octane, N-methyl-N'-dimethylaminoethylpiperazine, N,N-dimethylbenzylamine, bis-(N,N-diethylaminoethyl)-adipate, N,N-diethylbenzylamine, pentamethyldiethylenetriamine, N,N-dimethylcyclohexylamine, N,N,N',N'-tetramethyl-1,3-butanediamine, N,N-dimethyl-β-phenylethylamine, 1,2-dimethylimidazole and 2-methylimidazole.

Acid amides such as dimethylformamide, dimethylacetamide, and diethylformamide or urea derivatives such as tetramethylurea are also suitable catalysts. The addition of these catalysts to the reaction mixture is particularly advisable when aromatic halogen compounds which are comparatively inert towards nucleophilic substitution are used.

The nitrosubstituted aromatic phosphoric acid alkyl esters are generally prepared as follows: The aromatic halogen compound is introduced into the reaction vessel, if desired as a mixture with an inert solvent and/or catalyst. The trialkylphosphite is then added in small portions while maintaining the reaction mixture at a temperature of 0° to 150° C, preferably 50° to 120° C. The total quantity of phosphite added is about 0.9 to 3 mol, preferably 1 to 2 mol and most preferably 1 to 1.5 mol per mol of halogen compound. When the calculated quantity of alkyl halide has been formed (which can be checked, for example, by means of a gas meter), the reaction is stopped (if necessary with cooling) and any excess trialkylphosphite and solvent may be removed under vacuum or alternatively the reaction mixture may be extracted with petroleum ether after removal of the solvent.

If catalysts are used or if the aromatic halogen compounds are highly activated, the reactants may be mixed together in one step. In this variation of the process, however, it is necessary to ensure that the temperature of the reaction mixture is kept below 70° C and preferably below about 60° C in in order to avoid side reactions, (e.g. the reduction of nitro groups). In this case, the reaction is stopped when the calculated quantity of alkyl halide has been formed. One disadvantage of this method is the increased reaction time, but on the other hand the quantity of undesirable by-products is generally less than that formed when elevated temperatures are employed with portionwise addition of the trialkylphosphite.

Phosphonus and phospinous acid alkyl esters may also be used in an analogous manner. One advantage of these compounds is their higher reactivity compared with that of aromatically bound halogen. According to the invention, however, it is preferred to use phosphorous acid esters because they are generally more readily available.

The polyamines according to the invention are used as reactive components together with polyisocyanates, high molecular weight and/or low molecular weight polyols and optionally other compounds containing groups which are reactive with isocyanates for the production of polyurethanes. Examples of their use in the production of polyurethane lacquers, foils, coatings, elastomers and sealing compounds or fillers, but they are preferably used for the production of polyurethane foams. In order to ensure sufficient flame resistance, the polyamines according to the invention are used in such amounts that the finished polyurethane contains at least 0.5% by weight and preferably 1 to 5% by weight of phosphorus.

Another object of this invention is therefore to provide a process for the preparation of polyurethane from polyisocyanates, high molecular weight and/or low molecular weight polyols and other compounds containing groups which are reactive with isocyanates, characterized in that the compounds which are reactive with isocyanates include those of the general formula:

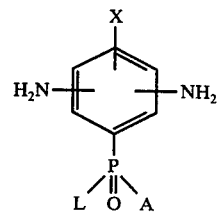

wherein A, L and X have the meaning indicated above, and which are used in such an amount that the polyurethane contains at least 0.5% by weight of phosphorus.

The isocyanates which may be used as starting components according to the invention include aliphatic, cycloaliphatic, araliphatic, aromatic and heterocyclic polyisocyanates as described in, for example, W. Siefken in Justus Liebigs Annalen der Chemie, 562, pages 75 to 136. Examples include ethylene diisocyanates; tetramethylene-1,4-diisocyanate; hexamethylene-1,6-diisocyanate; dodecane-1,12-diisocyanate; cyclobutane-1,3-diisocyanate; cyclohexane-1,3- and -1,4-diisocyanate and mixtures of these isomers, 1-isocyanato-3,3,5-trimethyl-5-isocyanatomethyl cyclohexane, (see e.g., U.S. Pat. No. 3,401,190); hexahydrotolylene-2,4- and -2,6-diisocyanate and mixtures of these isomers; hexahydrophenylene-1,3- and/or 1,4-diisocyanate; perhydrodiphenylmethane-2,4'- and/or 4,4'-diisocyanate; phenylene-1,3- and -1,4-diisocyanate; tolylene-2,4- and -2,6-diisocyanate and mixtures of these isomers; diphenylmethane-2,4'- and/or 4,4'-diisocyanate; naphthylene-1,5-diisocyanate; triphenylmethane-4,4',4''-triisocyanate; polyphenylpolymethylenepolyisoxyanates which can be obtained by aniline formaldehyde condensation followed by phosgenation and which have been described in British Pat. Nos. 874,430 and 848,671, m and p-isocyanatophenylsulphonylisocyanates as described in U.S. Pat. No. 3,454,606; perchlorinated arylpolyisocyanates as described in U.S. Pat. No. 3,277,138, polyisocyanates which contain carbodiimide groups as described in U.S. Pat. No. 3,152,162, the diisocyanates described in U.S. Pat. No. 3,493,330, polyisocyanates which contain allophanate groups as described in British Pat. No. 994,890, Belgian Pat. No. 761,626 and published Dutch Patent Application No. 7,102,524; polyisocyanates which contain isocyanaurate groups as described in U.S. Pat. No. 3,001,973, German Pat. Nos. 1,022,789; 1,222,067 and 1,027,394; and German Offenlegungsschriften Nos. 1,929,034 and 2,004,048; polyisocyanates which contain urethane groups as described in Belgian Pat. No. 752,261 or U.S. Pat. No. 3,394,164; polyisocyanates which contain acylated urea groups as described in German Pat. No. 1,230,778; polyisocyanates which contain biuret groups as described in U.S. Pat. Nos. 3,124,605 and 3,201,372 and British Pat. No. 889,050; polyisocyanates prepared by telomerization reactions as described in U.S. Pat. No. 3,654,106; polyisocyanates which contain ester groups such as those mentioned in British Pat. Nos. 965,474 and 1,072,956, U.S. Pat. No. 3,567,763 and German Pat. No. 1,231,688, and reaction products of the above mentioned isocyanates with acetals as described in German Pat. No. 1,072,385 as well as polyisocyanates which contain polymeric fatty acid groups as described in U.S. Pat. No. 3,455,883.

The distillation residues which are obtained from the production of isocyanates and which still contain isocyanate groups may also be used, optionally dissolved in one or more of the polyisocyanates mentioned above. Any mixtures of the above mentioned polyisocyanates may also be used.

It is generally preferred to use readily available polyisocyanates such as tolylene-2,4- and 2,6-diisocyanates and mixtures of these isomers ("TDI"); polyphenyl-polymethylene-polyisocyanates which can be obtained by aniline formaldehyde condensation followed by phosgenation ("crude MDI"), and polyisocyanates which contain carbodiimide groups, urethane groups, allophanate groups, isocyanurate groups, urea groups or biuret groups ("modified polyisocyanates").

The starting components to be used according to the invention also include compounds which contain at least two hydrogen atoms which are capable of reacting with isocyanates and which generally have a molecular weight of 400 to 10,000. In addition to compounds which contain amino groups, thiol groups or carboxyl groups, the compounds of this kind are in particular polyhydroxyl compounds, especially compounds having a molecular weight of 600 to 8000, preferably 800 to 6000, which contain 2 to 8 hydroxyl groups. Examples of such compounds include polyesters, polyethers, polythioethers, polyacetals, polycarbonates or polyester amides having at least 2, generally 2 to 8 and preferably 2 to 4 hydroxyl groups, of the kind which are generally known for the manufacture of both homogeneous and cellular polyurethanes.

Suitable polyesters having hydroxyl groups include the reaction products of polyhydric alcohols (preferably dihydric alcohols with the optional addition of trihydric alcohols) and polybasic, preferably dibasic carboxylic acids. Instead of free polycarboxylic acids, the corresponding polycarboxylic acid anhydrides or corresponding polycarboxylic acid esters of lower alcohols or mixtures thereof may be used for preparing the polyesters. The polycarboxylic acids may be aliphatic, cycloaliphatic, aromatic and/or heterocyclic and may be substituted, for example with halogen atoms, and/or unsaturated. The following are mentioned as examples: succinic acid; adipic acid; suberic acid; azelaic acid; sebacic acid; phthalic acid; isophthalic acid; trimellitic acid, phthalic acid anhydride; tetrahydrophthalic acid anhydride; hexahydrophthalic acid anhydride; tetrachlorophthalic acid anhydride; endomethylene-tetrahydrophthalic acid anhydride; glutaric acid; maleic acid; maleic acid anhydride; fumaric acid; dimeric and trimeric fatty acids such as oleic acid, if desired mixed with monomeric fatty acids, dimethylterephthalate or terephthalic acid bisglycol ester. Suitable polyhydric alcohols include ethylene glycol; propylene-1,2- and -1,3-glycol, butylene-1,4- and -2,3-glycol, hexane-1,6-diol, octane-1,8-diol, neopentyl glycol, cyclohexane dimethanol (1,4-bis-hydroxymethylcyclohexane), 2-methyl-1,3-propane-diol; glycerol; trimethylolpropane; hexane-1,2,6-triol; butane-1,2,4-triol; trimethylolethane; pentaerythritol; quinitol; mannitol and sorbitol; methyl glycoside; diethyleneglycol; triethyleneglycol; tetraethyleneglycol; polyethyleneglycols; dipropyleneglycol; polypropyleneglycols; dibutylene glycol and polybutyleneglycol. The polyesters may contain a proportion of carboxyl groups in end positions. Polyesters of lactones such as ε-caprolactone or hydroxycarboxylic acids such as ω-hydroxycaproic acid may also be used.

The polyethers having at least 2, generally 2 to 8 and preferably 2 to 3 hydroxyl groups which may be used according to the invention are also known per se and are prepared, for example, by the polymerization of epoxides such as ethylene oxide, propylene oxide, butylene oxide, tetrahydrofuran, styrene oxide or epichlorohydrin. Each may be prepared on its own, e.g., in the presence of $BF_3$, or by chemical addition of these epoxides, if desired as mixtures or successively, to starting components which contain reactive hydrogen atoms, such a water, alcohols or amines, e.g. ethylene glycol, propylene-1,3- or -1,2-glycol, trimethylol propane, 4,4'-dihydroxydiphenylpropane, aniline, ammonia, ethanolamine or ethylene diamine. Sucrose polyethers such as those described in for example, German Auslegeschriften No. 1,176,358 and No. 1,064,938, may also be used according to the invention. It is frequently preferred to use those polyethers which contain predominant amounts of primary OH groups (up to 90% by weight, based on all the OH groups present in the polyether). Polyethers modified with vinyl polymers, e.g. those obtained by the polymerization of styrene and acrylonitrile in the presence of polyethers (U.S. Pat. Nos. 3,383,351; 3,304,273; 3,523,093 and 3,110,695 and German Pat. No. 1,152,536) and polybutadienes which contain OH groups are also suitable.

Suitable polythioethers include in particular the condensation products obtained by the condensation of thiodiglycol either on its own and/or with other glycols, dicarboxylic acids, formaldehyde, aminocarboxylic acids or amino alcohols. The products obtained are polythio mixed ethers, polythio ether esters or polythioether ester amides, depending on the cocomponents.

Suitable polyacetals include the compounds which can be prepared from glycols such as diethylene glycol, triethylene glycol, 4,4'-dioxethoxy-diphenyldimethylmethane, hexanediol and formaldehyde. Polyacetals suitable for the purpose of the invention may also be prepared by the polymerization of cyclic acetals.

Suitable polycarbonates having hydroxyl groups include those known per se, e.g. those which can be prepared by the reaction of diols such as propane-1,3-diol, butane-1,4-diol and/or hexane-1,6-diol or diethyleneglycol, triethyleneglycol or tetraethyleneglycol with diarylcarbonates such as diphenylcarbonate or phosgene.

Suitable polyesteramides and polyamides include such compounds as the predominantly linear condensates obtained from polyvalent saturated and unsaturated carboxylic acids or their anhydrides and polyvalent saturated and unsaturated amino alcohols, diamines, polyamines and their mixtures.

Polyhydroxyl compounds which already contain urethane or urea groups and modified or unmodified natural polyols such as castor oil, carbohydrates or starch are also useful. Addition products of alkylene oxides with phenolformaldehyde resins or with urea formaldehyde resins may also be used according to the invention.

Examples of these compounds which may be used according to the invention have been described in High Polymers, Vol. XVI, "Polyurethanes, Chemistry and Technology" by Saunders-Frisch, Interscience Publishers, New York, London, Volume I, 1962, pages 32-42 and pages 44-54 and Volume II, 1964, pages 5-6 and 198-199 and in Kunststoff-Handbuch, Volume VII, Vieweg-Hochtlen, Carl-Hanser-Verlag, Munich, 1966, e.g. on pages 45 to 71.

Compounds having a molecular weight of 32 to 400 which contain at least two hydrogen atoms capable of reacting with isocyanates may also be used as starting compounds according to the invention. These are also compounds which contain hydroxyl groups and/or amino groups and/or thiol groups and/or carboxyl groups, preferably hydroxyl groups and/or amino groups, and they act as chain lengthening agents or cross-linking agents. These compounds generally contain 2 to 8 hydrogen atoms capable of reacting with isocyanates, and preferably 2 or 3 reactive hydrogen atoms. The following are mentioned as examples of such compounds: ethylene glycol; propylene-1,2- and -1,3-glycol, butylene-1,4- and -2,3-glycol, pentane-1,5-diol, hexane-1,6-diol, octane-1,8-diol, neopentyl glycol, 1,4-hydroxymethylcyclohexane, 2-methyl-1,3-propanediol, glycerol, trimethylolpropane, hexane-1,2,6-triol, trimethylolethane, pentaerythritol, quinitol, mannitol and sorbitol, diethyleneglycol, triethyleneglycol, tetraethyleneglycol, polyethyleneglycols having a molecular weight up to 400, dipropyleneglycols, polypropylene glycols having a molecular weight up to 400, dibutylene glycol, polybutylene glycols having a molecular weight up to 400, 4,4'-dihydroxydiphenylpropane, dihydroxy-methylhydroquinone, ethanolamine, diethanolamine, triethanolamine, 3-aminopropanol, ethylenediamine, 1,3-diaminopropane, 1-mercapto-3-aminopropane, 4-hydroxyphthalic acid or 4-aminophthalic acid, succinic acid, adipic acid, hydrazine, N,N'-dimethylhydrazine and 4,4'-diaminodiphenylmethane.

Water and/or readily volatile organic substances may be used according to the invention as blowing agents. Suitable organic blowing agents include acetone, ethyl acetate, halogenated alkanes such as methylene chloride, chloroform, ethylidene chloride, vinylidene chloride, monofluorotrichloromethane, chlorodifluoromethane and dichlorodifluoromethane as well as butane, hexane, heptane and diethylether. The effect of a blowing agent can also be obtained by the addition of compounds which decompose at temperatures above room temperature to liberate gasses. Such compounds include nitrogen, e.g. azo compounds such as azoisobutyric acid nitrile. Other examples of blowing agents and details concerning the use of blowing agents may be found in Kunststoff Handbuch, Volume VII, published by Vieweg and Hochtlen, Carl-Hanser-Verlag, Munich 1966, e.g. on pages 108 and 109, 453 to 455 and 507 to 510.

Catalysts are frequently used in the process according to the invention. Suitable catalysts include those known per se, e.g. tertiary amines such as triethylamine, tributylamine, N-methylmorpholine, N-ethylmorpholine, N-cocomorpholine N,N,N',N'-tetramethyl-ethylenediamine, 1,4-diaza-bicyclo(2,2,2)-octane, N-methyl-N'-dimethyl-aminoethyl-piperazine, N,N-dimethylbenzylamine, bis-(N,N-diethylaminoethyl)-adipate, N,N-diethylbenzylamine, pentamethyldiethylenetriamine, N,N-dimethylcyclohexylamine, N,N,N',N'-tetramethyl-1,3-butanediamine, N,N-dimethyl-β-phenylethylamine, 1,2-dimethylimiadazole and 2-methylimidazole. Mannich bases known per se which have been obtained from secondary amines such as dimethylamine and aldehydes, preferably formaldehyde, or ketones such as acetone, methyl ethyl ketone or cyclohexanone and phenols, such as phenol, nonyphenol or bis-phenol may also be used as catalysts.

Catalysts in the form of tertiary amines which contain hydrogen atoms capable of reacting with isocyanate groups include e.g. triethanolamine, triisopropanolamine, N-methyldiethanolamine, N-ethyldiethanolamine and N,N-dimethyl-ethanolamine and their reaction products with alkylene oxides such as propylene oxide and/or ethylene oxide.

Silaamines containing carbon-silicon bonds as described in U.S. Pat. No. 3,620,984 may also be used as catalysts. These include 2,2,4-trimethyl-2-silamorpholine or 1,3-diethylaminomethyl-tetramethyl-disiloxane.

Bases which contain nitrogen such as tetraalkylammonium hydroxides, alkali metal hydroxides such as sodium hydroxide, alkali metal phenolates such as sodium phenolate and alkali metal alcoholates such as sodium methylate may also be used as catalysts. Hexahydrotriazines are also suitable catalysts.

Organic metal compounds may also be used as catalysts particularly organic tin compounds. The organic tin compounds used are preferably tin (II) salts of carboxylic acids, such as tin (II) acetate, tin (II) octoate, tin (II) ethyl hexoate and tin (II) laurate; and tin (IV) compounds such as dibutyl tin oxide, dibutyl tin dichloride, dibutyl tin diacetate, dibutyl tin dilaurate, dibutyl tin maleate and dioctyl tin diacetate. All the catalysts mentioned above may, of course, be used as mixtures.

Other examples of catalysts to be used according to the invention and details concerning the action of these catalysts may be found in Kunststoff-Handbuch, Volume VII, published by Vieweg and Hochtlen, Carl-Hanser-Verlag, Munich 1966, e.g. on pages 96-102.

The catalysts are generally used in a quantity of between about 0.001 and 10% by weight, based on the quantity of compounds having a molecular weight of 400 to 10,000 which contain at least two hydrogen atoms capable of reacting with isocyanates.

Surface active additives such as emulsifiers and foam stabilizers may also be used according to the invention. Suitable emulsifiers include the sodium salts of ricinoleic sulphonates or salts of fatty acids with amines such as oleic acid diethylamine or stearic acid diethanolamine. Alkali metal or ammonium salts of sulphonic acids such as dodecylbenzenesulphonic acid or dinaphthylmethane disulphonic acid or of fatty acids such as ricinoleic acid or of polymeric fatty acids may also be used as surface-active additives.

The foam stabilizers used are mainly polyethersiloxanes, especially those which are water-soluble. These compounds generally have a polydimethylsiloxane group attached to a copolymer of ethylene oxide and propylene oxide. Foam stabilizers of this kind have been described in, for example, U.S. Pat. Nos. 2,834,748, 2,971,480 and 3,629,308.

Other substances which may also be added according to the invention include reaction retarders such as compounds which are acidic in reaction, e.g. hydrochloric acid or organic acid halides, cell regulators of a kind known per se such as paraffins, fatty alcohols or dimethylpolysiloxanes, pigments or dyes, stabilizers against ageing and weathering, plasticizers, fungistatic and bacteriostatic substances and fillers such as barium sulphate, kieselguhr, carbon black or whiting.

Other examples of surface-active additives, foam stabilizers, cell regulators, reaction retarders, stabilizers, plasticizers, dyes, fillers and fungistatic and bacteriostatic substances which may be used according to the invention and details concerning methods of using these additives and their action have been described in Kunststoff-handbuch, Volume VII, published by Vieweg and Hochtlen, Carl-Hanser-Verlag, Munich 1966, e.g. on pages 103 to 113.

According to the invention, the starting materials are reacted by the known one-step process, prepolymer process or semiprepolymer process, in many cases using mechanical devices such as those described in U.S. Pat. No. 2,764,565. Details concerning processing apparatus which may also be used according to the invention may be found in Kunststoff-Handbuch, Volume VII, published by Vieweg and Hochtlen, Carl-Hanser-Verlag, Munich 1966, e.g on pages 121 to 205.

When foams are to be produced according to the invention, foaming is frequently carried out in molds, i.e. the reaction mixture is introduced into a mold which may be made of a metal, e.g. aluminum, or a synthetic resin, e.g. an epoxide resin, and the foamable reaction mixture foams up inside the mold to form the molded product. The process of foaming inside the mold may be carried out in such a manner that a cellular structure is obtained on the surface of the molded product or it can be carried out to produce a molded product having a compact skin and cellular core. According to the invention, the quantity of foamable reaction mixture introduced into the mold may be just sufficient to enable the resulting foam to fill up the mold, or if desired a large quantity of foamable reaction mixture may be introduced, in which case the process employed is known as overcharging. This method has already been disclosed in, for example, U.S. Pat. Nos. 1,178,490 and 3,182,104.

So-called external mold release agents known per se e.g. silicone oils, are frequently used for the process of foaming in the mole. Alternatively, so-called internal mold release agents such as those disclosed in, for example, German Offenlegungsschirften No. 2,121,670 and 2,307,589 may be used, if desired as mixtures with external mold release agents.

Cold setting foams may also be produced according to the invention (see British Pat. No. 1,162,517, and German Offenlegungsschrift No. 2,153,086).

Foams may, of course, also be produced by the process of block forming or by the double conveyor belt process known per se.

The following examples serve to explain the present invention. The parts and percentages given represent parts by weight or percentages by weight unless otherwise indicated.

EXAMPLE 1

2,6-Diamino-4-carbomethoxy-benzene-phosphonic acid dimethyl ester 45 g of (0.134 mol) of 2,6-dinitro-4-carbomethoxybenzene-phosphonic acid dimethylester are dissolved in 550 ml of methanol and hydrogenated at 35° C and 60 excess atmospheres after the addition of 10 g of Raney nickel. The catalyst is filtered off after 4 hours and the solvent is then evaporated off and the residue is freed from any remaining solvent in a high vacuum.

Yield: 32 g   82% of the theoretical, m.p.: 150°–151° C. The IR and NMR spectra confirm its identify.

EXAMPLE 2

2,6-Diamino-4-carbomethoxy-benzene-phosphonic acid diethyl ester

The following compounds are used in a manner analogous to Example 1:

80 g (0.221 mol) of 2,6-dinitro-4-carbomethoxy-benzene-phosphonic acid diethylester, 1000 ml of ethanol and 15 g of Raney nickel.

Yield: 61 g   91% of the theoretical, m.p.: 105°–107° C. The IR and nuclear resonance spectra confirm the chemical structure of the reaction product.

EXAMPLE 3

2,6-Diamino-4-carboisobutoxy-benzene-phosphonic acid diethyl ester 108 g (0.268) of 2,6-dinitro-4-carboisobutoxy-benzene-phosphonic acid diethylester in 1000 ml of ethanol are reduced with 20 g of Raney nickel at 50° to 60° C and 70 excess atmospheres by the method described in Example 1. The hydrogenation time is 3 hours.

Yield: 86 g   93% of the theoretical, m.p.: 48°–50° C. The IR and nuclear resonance spectra confirm the identity of the product.

EXAMPLE 4

2,4-Diamino-benzene-phosphonic acid-dimethyl ester (1)

113.5 g (0.479 mol) of 2,4-dinitro-benzene-phosphonic acid dimethyl ester (1) dissolved in 1500 ml of methanol are hydrogenated at 35° C and 60 excess atmospheres in the presence of 25 g of Raney nickel.

Yield after crystallization of the crude product from toluene: 61 g   59% of the theoretical, m.p.: 140°–141° C. The IR and NMR spectrum and analysis of elements confirm the identity of the reaction product.

Calculated: C, 44.4; H, 6.0; N, 12.95; P, 14.35. Found: C, 44.3; H, 6.0; N, 13.0; P, 14.3.

EXAMPLE 5

A mixture of the following components is reacted in a closed mold:

100 Parts by weight of a polypropylene glycol having an OH number of 28 which has been started on trimethylolpropane and modified with ethylene oxide to result in 60% of primary hydroxyl end groups, 3.1 parts by weight of N-methylmorpholine, 0.5 parts by weight of N,N-dimethyl-ethanolamine, 1.0 parts by weight of a silicone stabilizer according to the general formula

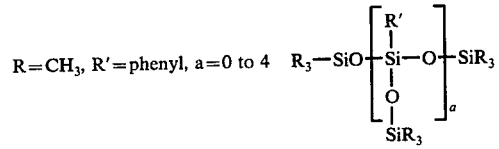

$R=CH_3$, $R'=$phenyl, $a=0$ to $4$ 5.0 parts by weight of 2,6-diamino-4-carboisobutoxy-benzenephosphonic acid diethyl ester, and 465 parts by weight of the polyisocyanate described below: 20 Parts of 1,2-propylene glycol are added to a mixture of 225 parts of a mixture of 80% by weight of 2,4-tolylenediisocyanate and 20% by weight of 2,6-tolylenediisocyanate and 274 parts of 4,4'-diphenylmethane diisocyanate at 60° C and the resulting mixture is reacted inside a metal mold for 30 minutes. The temperature is raised to 130° C after the addition of 1 part of β-phenyl ethylethyleneamine. The trimerization reaction which occurs at this temperature is stopped after 2½ hours, when the NCO content of the reaction mixture is 26.5%, by the addition of 1 part of methyl p-toluenesulphonate.

The polyisocyanate obtained after diultion with 624 parts of an 80/20 mixture of 2,4- and 2,6-tolylene diisocyanate has an NCO content of 38.4% by weight, a viscosity of 24 cP at 25° C and a refractive index $n_D^{50}$ = 1,5738.

A foam which has the following mechanical properties is obtained:

| Gross density | (DIN 53 420) | 36 kg/m³ |
| Tensile test | (DIN 53 571) | 100 KPa |
| Elongation at break | (DIN 53 571) | 110% |
| Pressure test | (DIN 53 577) | 4.5 KPa |
| Pressure deformation residue | (DIN 53 572) | 7.9% |

What is claimed is:

1. In a process for the preparation of polyurethanes comprising reacting polyisocyanates, high molecular weight and/or low molecular weight polyols and other organic compounds which contain groups capable of reacting with isocyanates, the improvement wherein the compounds which are reactive with isocyanate groups, include compounds of the following formula, used in an amount such that the polyurethane contains at least 0.5% by weight of phosphorous:

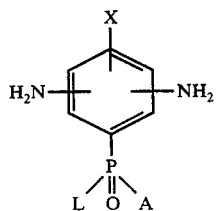

wherein
 A and L, which are identical or different, represent optionally branched $C_1$-$C_{17}$ alkyl group or -OR group wherein R represents an optionally branched $C_1$-$C_8$-alkyl group, and
X represents hydrogen, halogen, an optionally branched $C_1$-$C_8$ alkyl group, a $C_6$-$C_{12}$ aryl or aralkyl groups, $NH_2$, $CF_3$, CN, COOR', $SO_3R'$,

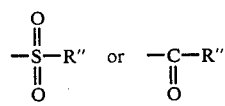

wherein:
 R' represents hydrogen or an optionally branched alkyl or cycloalkyl group having 1–10 C atoms and
 R" represents an optionally branched alkyl or cycloalkyl group having 1–10 C atoms.

2. The process of claim 1, wherein A and B represent an -OR group in which
 R represents an optionally branched $C_1$-$C_4$ alkyl group, and X represents hydrogen, chlorine, $CH_3$, $NH_2$, or COOR'
wherein:
 R' represents an optionally branched $C_1$-$C_4$ alkyl group.

3. The process of claim 1, wherein compounds of the following formula are used:

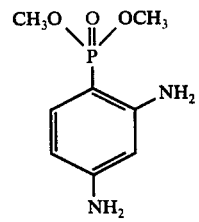

4. The process of claim 1, wherein compounds of the following formula are used:

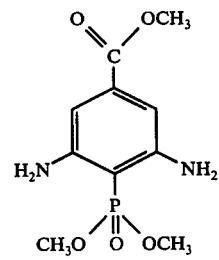

5. The process of claim 1, wherein compounds of the following formula are used:

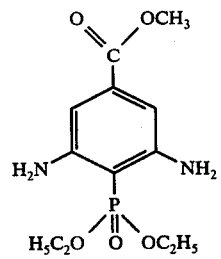

6. The process of claim 1, wherein compounds of the following formula are used:

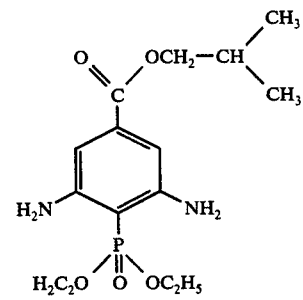

* * * * *